US011400312B2

(12) United States Patent
Qiu et al.

(10) Patent No.: US 11,400,312 B2
(45) Date of Patent: Aug. 2, 2022

(54) ENDOSCOPE DEVICE

(71) Applicant: SONOSCAPE MEDICAL CORP., Guangdong (CN)

(72) Inventors: Jianjun Qiu, Guangdong (CN); Yunliang Chen, Guangdong (CN); Nengyun Feng, Guangdong (CN); Erwei Dong, Guangdong (CN)

(73) Assignee: SONOSCAPE MEDICAL CORP., Guangdong (CN)

( * ) Notice: Subject to any disclaimer, the term of this patent is extended or adjusted under 35 U.S.C. 154(b) by 91 days.

(21) Appl. No.: 16/914,342

(22) Filed: Jun. 27, 2020

(65) Prior Publication Data

US 2020/0391046 A1    Dec. 17, 2020

Related U.S. Application Data

(63) Continuation of application No. PCT/CN2018/121957, filed on Dec. 19, 2018.

(30) Foreign Application Priority Data

Dec. 29, 2017    (CN) .......................... 201711478368.9

(51) Int. Cl.
*A61B 1/06*      (2006.01)
*A61B 1/00*      (2006.01)
(Continued)

(52) U.S. Cl.
CPC .......... *A61N 5/062* (2013.01); *A61B 1/00006* (2013.01); *A61B 1/00087* (2013.01);
(Continued)

(58) Field of Classification Search
CPC ............ A61B 1/00006; A61B 1/00087; A61B 1/0638; A61B 1/0661; A61B 1/043; A61N 5/0601
See application file for complete search history.

(56) References Cited

U.S. PATENT DOCUMENTS 5,043,803 A * 8/1991 Asaida ............... H04N 9/04515
348/E9.01
2002/0168317 A1* 11/2002 Daighighian .......... A61K 49/18
600/407
(Continued)

FOREIGN PATENT DOCUMENTS

CN      101744611 A     6/2010
CN      107137824 A     9/2017
(Continued)

OTHER PUBLICATIONS

International Search Report for PCT/CN2018/121957 dated Mar. 20, 2019, ISA/CN.

(Continued)

*Primary Examiner* — Aaron B Fairchild
(74) *Attorney, Agent, or Firm* — Yue (Robert) Xu; Apex Attorneys at Law, LLP

(57) ABSTRACT

An endoscope device is provided, including: a first light source section, a second light source section, an imaging section, and a light cut filter. The first light source section is configured to project illumination light to an object. The second light source section is configured to project treatment light to the object. The imaging section is configured to capture an image of the object using reflected light from the object. The light cut filter is arranged between the object and the imaging section and has a transmittance greater than zero and less than a transmittance upper threshold for the treatment light, where the transmittance upper threshold is predetermined based on a rule of avoiding image overexposure.

18 Claims, 11 Drawing Sheets

(51) Int. Cl.
*A61N 5/06* (2006.01)
*A61N 5/067* (2006.01)

(52) U.S. Cl.
CPC .............. *A61B 1/06* (2013.01); *A61B 1/0638* (2013.01); *A61B 1/0661* (2013.01); *A61N 5/0601* (2013.01); *A61N 5/067* (2021.08); *A61N 2005/063* (2013.01); *A61N 2005/0626* (2013.01); *A61N 2005/0651* (2013.01); *A61N 2005/0663* (2013.01); *A61N 2005/0667* (2013.01)

(56) References Cited

U.S. PATENT DOCUMENTS

| | | | |
|---|---|---|---|
| 2004/0160521 A1* | 8/2004 | Yamamoto | H04N 9/0451 348/222.1 |
| 2009/0244924 A1 | 10/2009 | Enomoto | |
| 2010/0145416 A1 | 6/2010 | Kang et al. | |
| 2011/0118547 A1 | 5/2011 | Erikawa | |
| 2018/0093104 A1 | 4/2018 | Ikeshita et al. | |

FOREIGN PATENT DOCUMENTS

| | | | |
|---|---|---|---|
| CN | 108014424 A | 5/2018 | |
| EP | 2433556 A1 | 3/2012 | |
| JP | 2006094907 A | 4/2006 | |
| JP | 2012-50601 A | * 3/2012 | ............... A61B 1/04 |
| JP | 2012050601 A | 3/2012 | |
| JP | 2012065899 A | 4/2012 | |
| WO | 2016158195 A1 | 10/2016 | |

OTHER PUBLICATIONS

The 3rd Office Action of Priority Application dated Jun. 2, 2020.

* cited by examiner

ENDOSCOPE DEVICE

This application is a continuation application of International Patent Application No. PCT/CN2018/121957, titled "ENDOSCOPE APPARATUS", filed on Dec. 19, 2018, which claims the priority to Chinese Patent Application No. 201711478368.9, titled "ENDOSCOPE DEVICE", filed on Dec. 29, 2017 with the Chinese Patent Office, both of which are incorporated herein by reference in their entireties.

TECHNICAL FIELD

The present disclosure relates to the technical field of endoscopes, and in particular to an endoscope device.

BACKGROUND

Photodynamic therapy (PDT) has been proven to be an effective method for treating malignant tumors and precancerous lesions. Clinical operations of the PDT include the following two main steps: (1) injecting a photosensitizer intravenously into a patient, which will be enriched in a lesion tissue after being metabolized in the body of the patient for hours or tens of hours; and (2) irradiating the lesion tissue with a certain dose of treatment light in a certain wavelength band according to spectral absorption characteristics of the photosensitizer.

The principle of treating tumors by PDT is as follows. After molecules of the photosensitizer enriched in the lesion tissue absorb photons, a energy state of the molecules is changed from a steady state to a high energy state. The molecules transfer energy to oxygen molecules (triplet oxygen $3O2$) in a biological tissue, so that the oxygen molecules (triplet oxygen $3O2$) are activated to form singlet oxygen ($1O2$) and superoxide anion radical ($O2-$). The singlet oxygen ($1O2$) and the superoxide anion radical ($O2-$) can strongly destroy various biological macromolecules in tumor cells, thereby causing the tumor necrosis and apoptosis, damaging microvascular endothelium of the tumor tissue to form micro thrombi, and ultimately destroying the tumor tissue.

Treatment light used in PDT can enter a body cavity via an optical fiber to irradiate the tumor tissue in the cavity. In addition, the PDT may be combined with an endoscope to monitor the process of treating tumors in the cavity in real time. If the PDT is combined with an endoscope, the treatment light of PDT may enter the body cavity via the optical fiber which passes through a surgical instrument passage of the endoscope to irradiate the tumor tissue, or the treatment light may be integrated into a cold light source in the endoscope, so that ordinary observation light and the treatment light of PDT are transmitted to an end of the endoscope via a same optical fiber of the endoscope to irradiate in the cavity.

A power of the treatment light of PDT may usually reach 1 W to 2 W, and a light power density of the treatment light of PDT may reach 0.1 $W/cm^2$ to 1 $W/cm^2$ when the treatment light irradiates a lesion area closely. Therefore, the problem in treating inter-cavity tumor by the PDT combined with the endoscope is that, intensity of treatment light reflected by an object and received by an image sensor far exceeds a linear response range of the image sensor, so that the image is overexposed and thus the PDT treatment process cannot be monitored in real time by using the endoscope.

In order to eliminate the problem of image overexposure caused by the treatment light, it is proposed to arrange a light cut filter between the object and an imaging section of the endoscope to cut off the treatment light. That is, the intensity of the treatment light reflected by the object and entering an image sensor of the imaging section is equal to zero. Although the problem of image overexposure can be eliminated in this way, the area of a treatment light spot cannot be observed in the image captured using reflected light from the object, maybe resulting in a problem that the PDT treatment cannot have a desired result due to incomplete coverage on the lesion area by the PDT treatment light spot.

SUMMARY

An endoscope device is provided according to the present disclosure. The endoscope device includes: a first light source section, a second light source section, an imaging section, and a light cut filter. The first light source section is configured to project illumination light to an object. The second light source section is configured to project treatment light to the object. The imaging section is configured to capture an image of the object using reflected light from the object. The light cut filter is arranged between the object and the imaging section and has a transmittance greater than zero and less than a transmittance upper threshold for the treatment light, where the transmittance upper threshold is predetermined based on a rule of avoiding image overexposure.

BRIEF DESCRIPTION OF THE DRAWINGS

The drawings to be used in the embodiments or the conventional technology are described briefly as follows, so that the technical solutions according to the embodiments of the present disclosure or according to the conventional technology become clearer. It is apparent that the drawings in the following description are only some embodiments of the present disclosure. For those skilled in the art, other drawings may be obtained according to these drawings without any creative work.

DETAILED DESCRIPTION

The technical solution according to the embodiments of the present disclosure will be described clearly and completely as follows in conjunction with the drawings. It is apparent that the described embodiments are only a few rather than all of the embodiments. Any other embodiments obtained by those skilled in the art based on the embodiments in the present disclosure without any creative work fall in the scope of the present disclosure.

Figure 1:
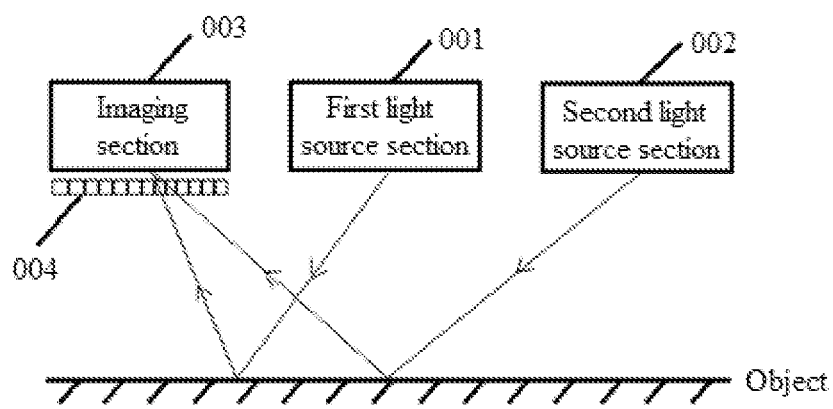
FIG. 1 is a schematic structural diagram of an endoscope device according to the present disclosure.

An endoscope device is provided according to an embodiment of the present disclosure. Referring to FIG. 1, the endoscope device includes: a first light source section 001, a second light source section 002, an imaging section 003, and a light cut filter 004.

The first light source section 001 is configured to project illumination light to an object.

The second light source section 002 is configured to project treatment light to the object.

The imaging section 003 is configured to capture an image of the object using reflected light from the object.

The light cut filter 004 is arranged between the object and the imaging section 003 and has a transmittance greater than zero and less than a transmittance upper threshold for the treatment light, where the transmittance upper threshold is predetermined based on a rule of avoiding image overexposure.

It can be seen that in the embodiment of the present disclosure, a light cut filter is arranged between the object and the imaging section, and the light cut filter has a transmittance greater than zero and less than a transmittance upper threshold for the treatment light, where the transmittance upper threshold is predetermined based on a rule of avoiding image overexposure. In this way, the problem of image overexposure caused by the treatment light can be avoided to ensure visualization of the photodynamic therapy process. Furthermore, a part of the treatment light can transmit through the light cut filter to reach the imaging section, to ensure that the image captured by the imaging section contains a treatment light spot area. Therefore, according to the treatment light spot area, medical personnel can adjust a size and a position of the spot of the treatment light in time to accurately cover the lesion area of the object, ensuring the clinical effect of the photodynamic therapy.

In an embodiment, the second light source section 002 may be a laser light source for projecting a red laser light to the object, where the red laser light has a central wavelength ranging from 610 nm to 690 nm.

In another embodiment, the second light source section 002 may be a Light Emitting Diode (LED) light source for projecting red narrow-band LED light to the object, where the red narrow-band LED light has a central wavelength ranging from 610 nm and 690 nm.

The treatment light, which has a central wavelength ranging from 610 nm to 690 nm and may be a laser light or a narrow-band LED light, can generate phototoxic substances at the lesion area in the object where the photosensitizer is enriched, and thus can kill cells in the lesion area.

In an embodiment, the first light source section 001 may include a white light source and a special light source.

The white light source is configured to project white light to the object. The special light source is configured to project special light to the object. The wavelength of the white light is in a wavelength range of visible light, and the wavelength of the special light is in a wavelength range corresponding to an absorption peak of hemoglobin.

In an embodiment, the special light projected by the special light source may include light having wavelengths around 415 nm and 540 nm corresponding to two absorption peaks of hemoglobin, but not include light having a wavelength above 600 nm.

In an embodiment, the endoscope device may be operated in different operation modes by controlling the operating states of the first light source section 001 and the second light source section 002. In the embodiment, an operation mode in which only the white light source operates is referred as a white light observation mode, an operation mode in which only the special light source operates is referred as a special light observation mode, an operation mode in which both the white light source and the second light source section 002 operate is referred as a white light observation along with photodynamic therapy mode, and an operation mode in which both the special light source and the second light source section 002 operate is referred as a special light observation along with photodynamic therapy mode.

Figure 2:
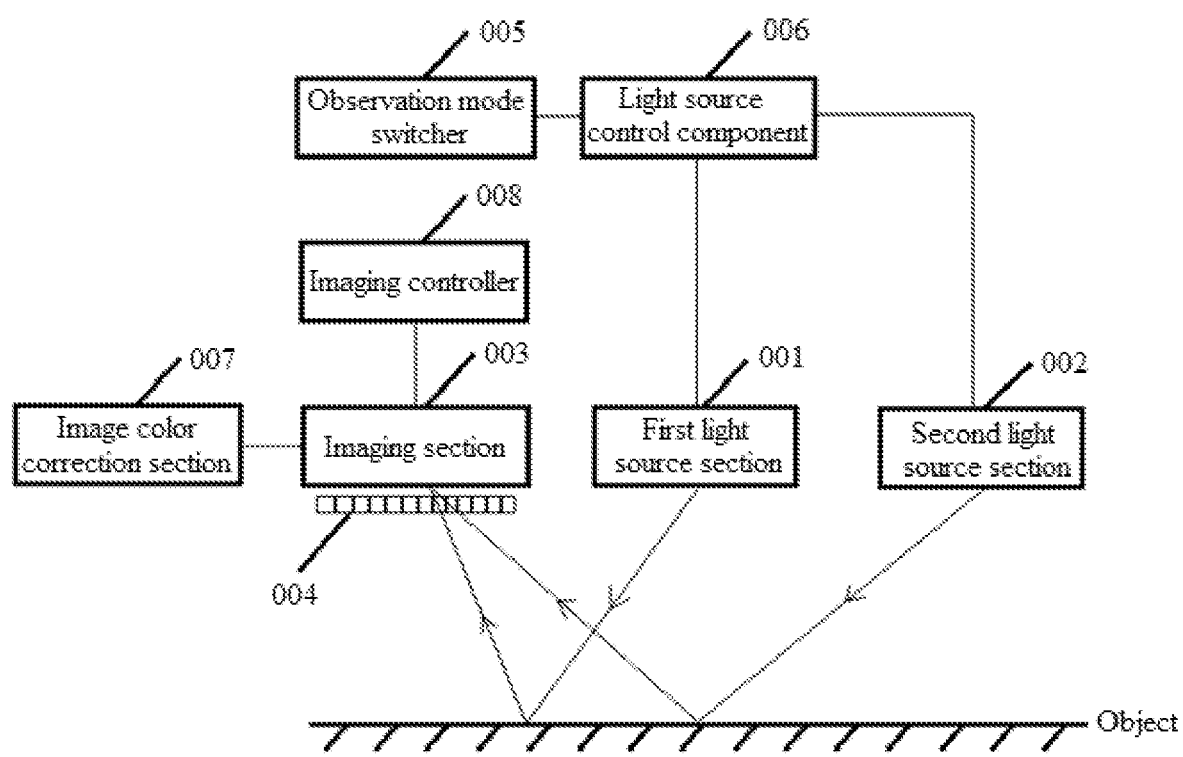
FIG. 2 is a detail schematic structural diagram of an endoscope device according to the present disclosure.

Referring to FIG. 2, in order for a convenient operation of the user to flexibly switch the operation mode of the endoscope device, the endoscope device in an embodiment may further include an observation mode switcher 005 and a light source control component 006.

The observation mode switcher 005 is arranged on the endoscope device. The light source control component 006 is configured to control the first light source section 001 and the second light source section 002 according to an operation mode selected by the user using the observation mode switcher 005. The operation mode includes the white light observation mode, the special light observation mode, the white light observation along with photodynamic therapy mode, or the special light observation along with photodynamic therapy mode.

In order to correct color deviation of an image which is caused by the light cut filter 004 filtering out some red-band light from the white light used for observation, the endoscope device according to an embodiment may further include an image color correction section 007.

The image color correction section 007 is configured to perform a color correction process on the image captured by the imaging section using a predetermined color correction matrix when the first light source section 001 projects the white light to the object. The color correction matrix is calculated by a least squares algorithm based on a difference between a first color expression result and a second color expression result. The first color expression result is obtained based on an image of the object which is captured using the white light filtered by the light cut filter 004. The second color expression result is obtained based on an image of the object which is captured directly using the white light.

Since the endoscope device according to the embodiment includes multiple light sources and has multiple working modes, images captured by the imaging section 003 may have different brightness. In order to prevent this situation, the endoscope device according to an embodiment may further include a dimming circuit and/or an imaging controller 008.

The dimming circuit is configured to determine a brightness value of a current image captured by the imaging section, and adjust a light source parameter of the first light source section 001 based on a difference between the brightness value and a predetermined brightness value. The imaging controller 008 is configured to determine a brightness value of a current image captured by the imaging section and adjust an imaging parameter of the imaging section based on a difference between the brightness value and a predetermined brightness value. In the embodiment, the dimming circuit may be a sub-circuit arranged in the light source control component 006.

The endoscope device according to an embodiment may further include a dedicated optical fiber. The dedicated optical fiber is arranged between the second light source section 002 and the object and configured to transmit the treatment light.

The dedicated optical fiber passes through a surgical instrument passage of the endoscope device and protrudes from a front end face of an insertion portion of the endoscope device.

The second light source section 002 according to an embodiment may further include a verification light source. The verification light source is configured to generate verification light having a wavelength different from that of the treatment light to verify whether the dedicated optical fiber is capable of transmitting light normally. By using the verification light having a wavelength different from that of the treatment light to verify whether the dedicated optical fiber is capable of transmitting light normally, most of the light energy of the verification light cannot be filtered out by the light cut filter, so that the verification light can be observed in the image captured by the imaging section.

Since the treatment light is normally in the red light band, but the human eye has low visual sensitivity to the light in the red light band and the near-infrared band, the wavelength of the verification light generated by the verification light source is less than the wavelength of the treatment light to further facilitate observation of the verification light in the image by the user. In addition, the verification light source may be a laser light source or a narrow-band LED light source.

In an embodiment, the light cut filter 004 has a transmittance greater than or equal to 0.1% and less than or equal to 1% for the treatment light.

Figure 3:
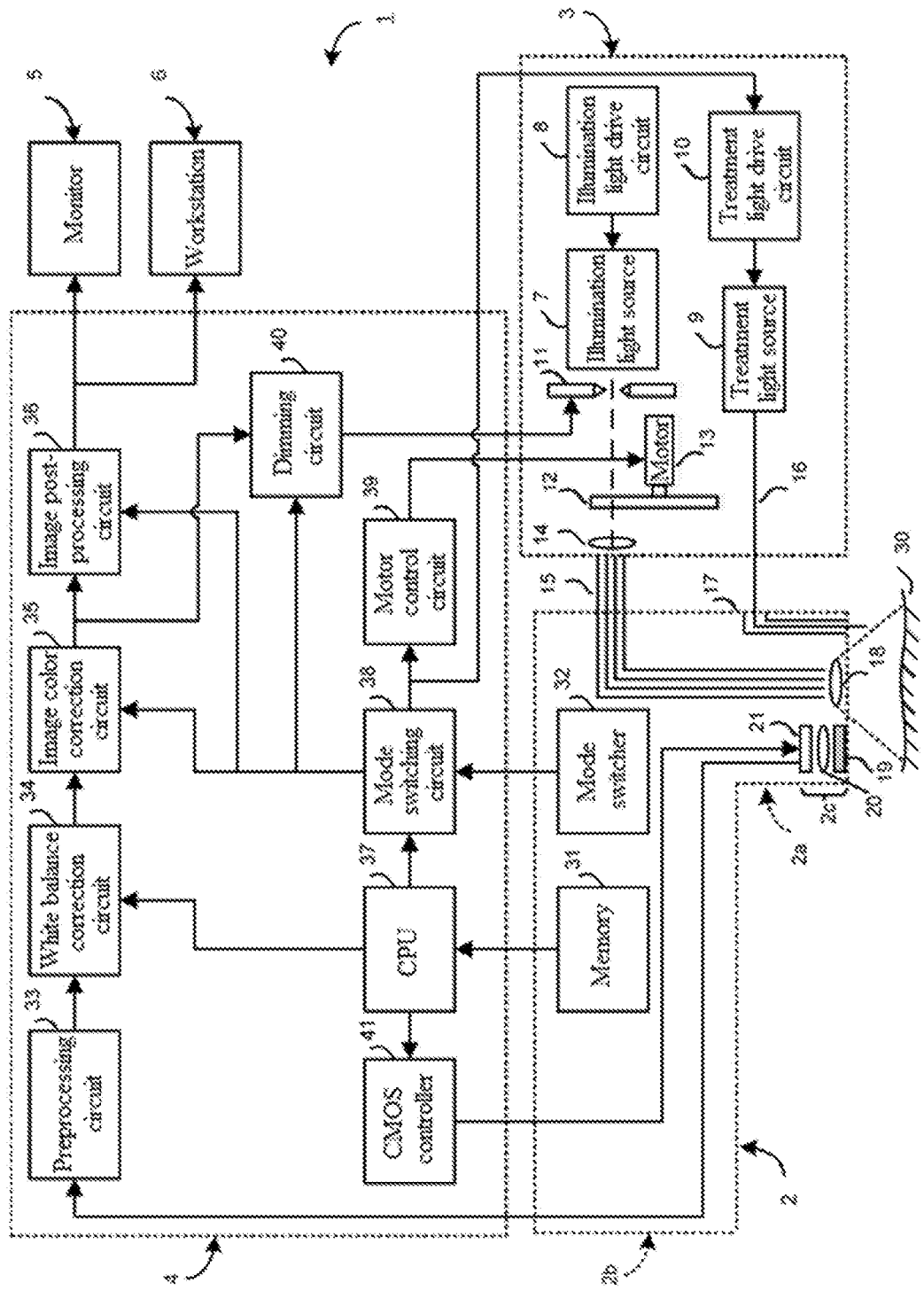
FIG. 3 is a schematic diagram of a main structure of an endoscope device according to an embodiment of the present disclosure.
Figure 4:
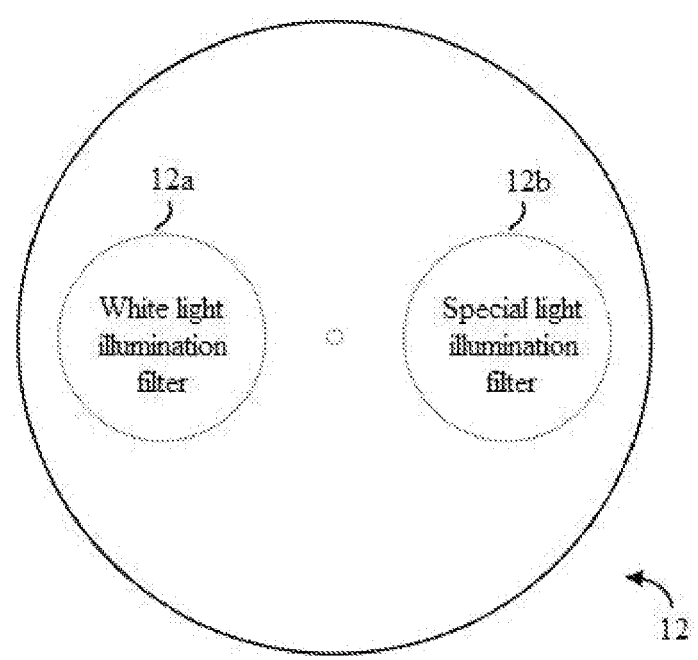
FIG. 4 is a detail schematic structural diagram of a rotation filter shown in FIG. 3 according to an embodiment.
Figure 5:
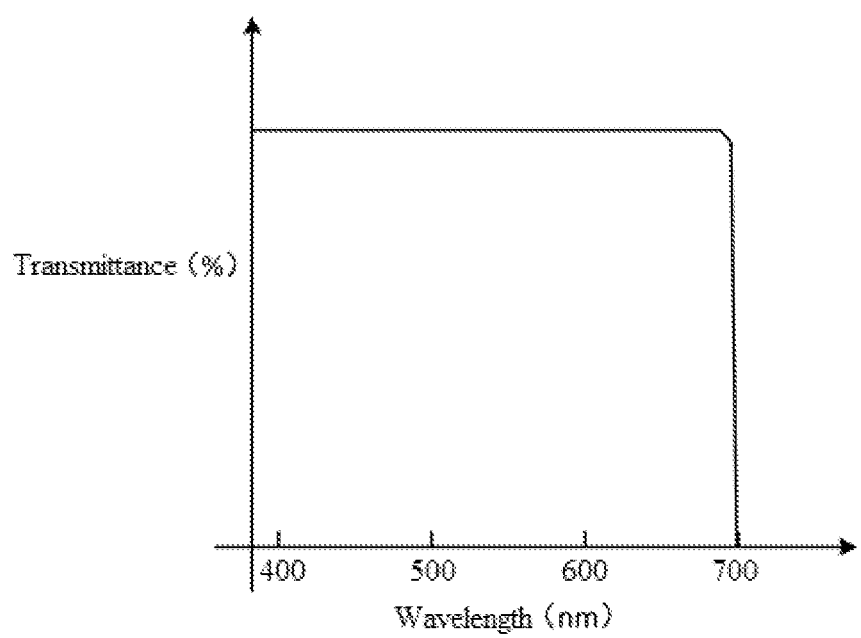
FIG. 5 is a schematic diagram showing transmittance characteristics of a white light illumination filter shown in FIG. 4 according to an embodiment.
Figure 6:
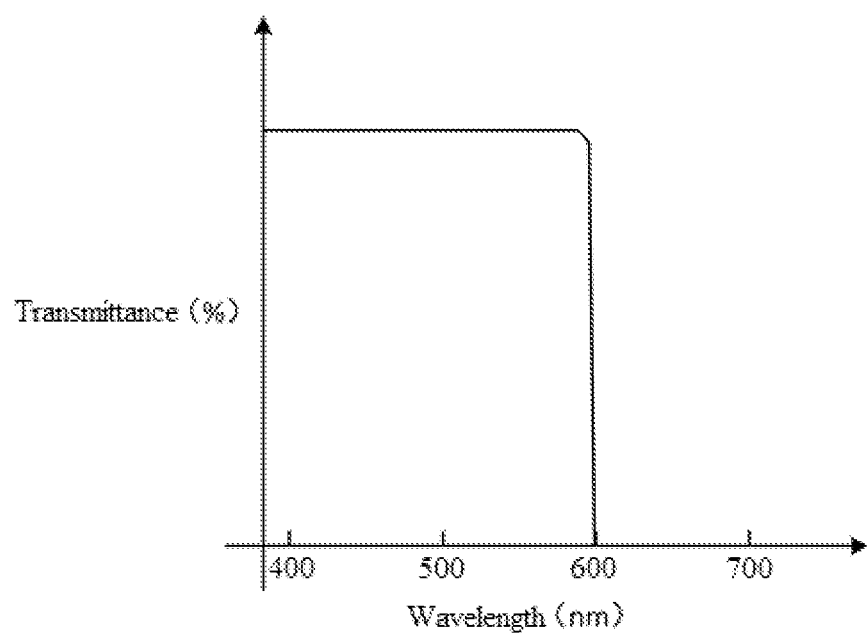
FIG. 6 is a schematic diagram showing transmittance characteristics of a special light illumination filter shown in FIG. 4 according to an embodiment.
Figure 7:
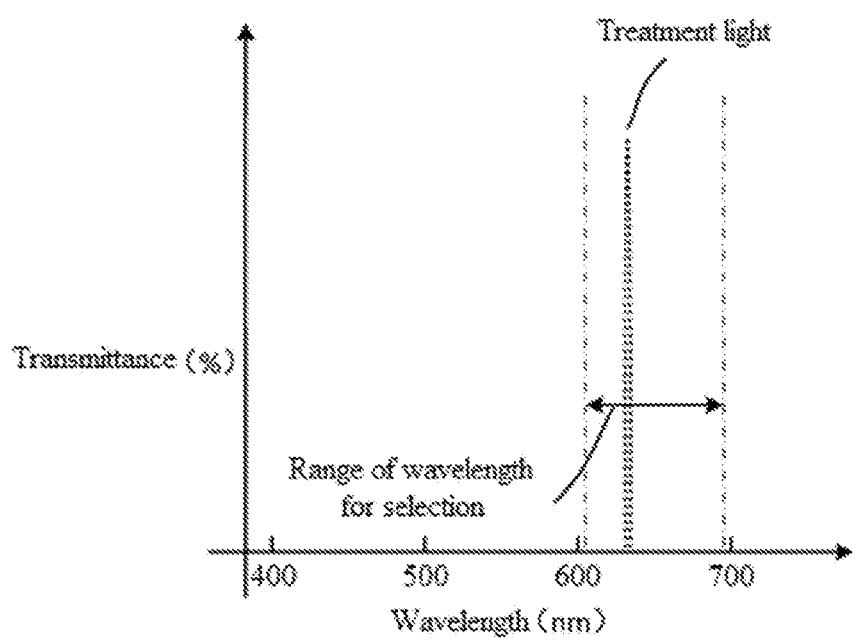
FIG. 7 is a schematic diagram showing a wavelength spectral band of treatment light emitted by a treatment light source shown in FIG. 3 according to an embodiment.
Figure 8:
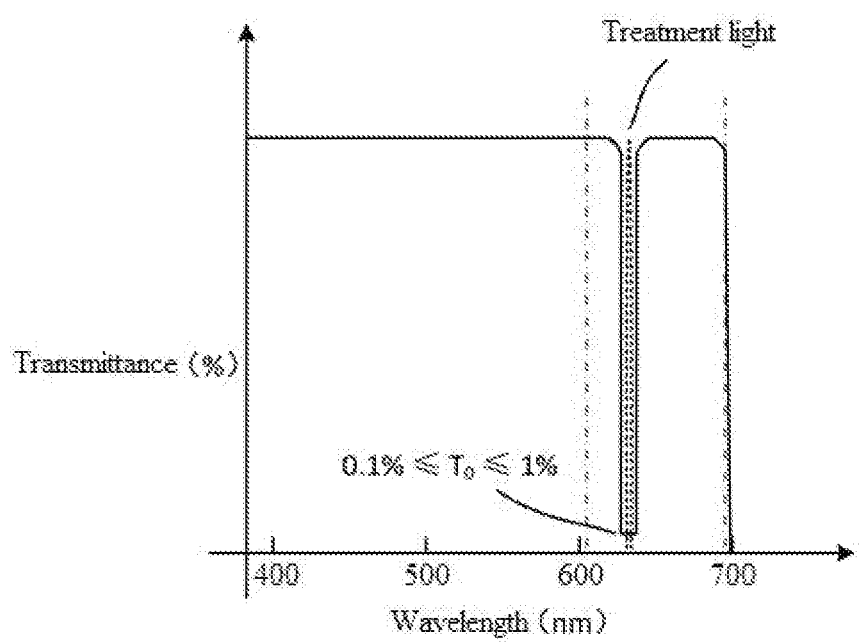
FIG. 8 is a schematic diagram showing transmittance characteristics of a treatment light cut filter shown in FIG. 3 according to an embodiment.
Figure 9:
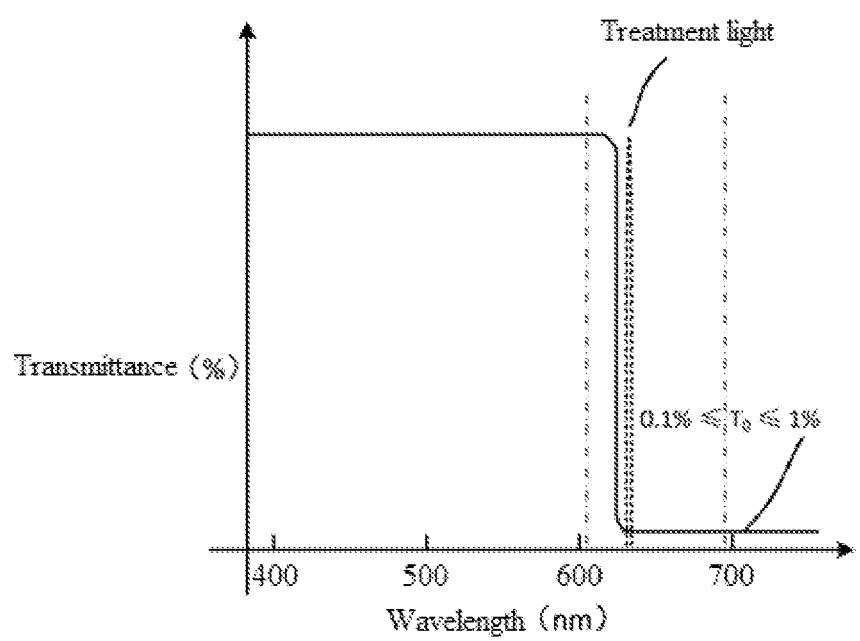
FIG. 9 is a schematic diagram showing transmittance characteristics of a treatment light cut filter shown in FIG. 3 according to an embodiment, which is different from that in FIG. 8.

Based on the above embodiments, an endoscope device is provided according to an embodiment of the present disclosure. Reference is made to FIG. 3 to FIG. 9, which show the technical solutions in the embodiment of the present disclosure. FIG. 3 is a schematic diagram of a main structure of an endoscope device according to an embodiment of the present disclosure. FIG. 4 is a detail schematic structural diagram of a rotation filter shown in FIG. 3 according to an embodiment. FIG. 5 is a schematic diagram showing transmittance characteristics of a white light illumination filter shown in FIG. 4 according to an embodiment. FIG. 6 is a schematic diagram showing transmittance characteristics of a special light illumination filter shown in FIG. 4 according to an embodiment. FIG. 7 is a schematic diagram showing a band of wavelength of treatment light emitted by a treatment light source shown in FIG. 3 according to an embodiment. FIG. 8 is a schematic diagram showing transmittance characteristics of a treatment light cut filter shown in FIG. 3 according to an embodiment. FIG. 9 is a schematic diagram showing transmittance characteristics of a treatment light cut filter shown in FIG. 3 according to an embodiment, which is different from that in FIG. 8.

As shown in FIG. 3, the endoscope device 1 according to the embodiment includes the following main parts: an endoscope 2, a light source apparatus 3, a processor 4, a monitor 5, and a workstation 6. The endoscope 2 can be inserted into a body cavity to capture images of an observation object 30 in the body cavity and output a captured signal to the processor 4. The light source apparatus 3 emits illumination light used for observation and treatment light used for treatment. The processor 4 is configured to perform a signal process on the captured signal outputted from the endoscope 2. The monitor 5 displays an image signal outputted from the processor 4. The workstation 6 is configured to perform a data archiving process on image data outputted from the processor 4.

The endoscope 2 includes an insertion portion 2a and a manipulation portion 2b. The insertion portion 2a is configured to be inserted into the body cavity. The manipulation portion 2b is arranged at a rear end of the insertion portion 2a. In addition, an optical fiber 15 passes through the insertion portion 2a to transmit illumination light emitted by the light source apparatus 3 to a front end portion 2c of the insertion portion 2a. At a rear end of the optical fiber 15, an optical fiber connector, which is not shown in FIG. 3, is arranged to detachably connect the optical fiber 15 to the light source apparatus 3. Based on the above structure, the illumination light emitted by the light source apparatus 3 is transmitted by the optical fiber 15 and then passes through a illumination lens 18 which is arranged at the front end portion 2c of the insertion portion 2a, to illuminate the observation object 30 in the body cavity at a certain divergence angle.

The light source apparatus 3 includes: an illumination light source 7, an illumination light drive circuit 8, a diaphragm 11, a rotation filter 12, a motor 13, and a condenser lens 14. The illumination light source 7 emits white light for illumination. The illumination light source 7 may be, for example, a xenon lamp. The illumination light drive circuit 8 is configured to drive the illumination light source 7 with a constant drive current. The diaphragm 11 is arranged on an exit light path of the illumination light source 7 and is controlled by the processor 4 to adjust the amount of white light emitted by the illumination light source 7. The rotation filter 12 is driven by the motor 13 according to an operation mode of the endoscope device 1, to rotate to arrange a white light illumination filter 12a or a special light illumination filter 12b, which are mounted on the rotation filter 12, to be on the exit light path of the illumination light source 7. The motor 13 is controlled by the processor 4 to rotate the rotation filter 12. The condenser lens 14 condenses illumination light which has been filtered by the rotation filter 12 and controls the condensed illumination light to irradiate an incident end surface of the optical fiber 15 which is connected to the light source apparatus 3.

In addition, the light source apparatus 3 further includes a treatment light source 9, a treatment light drive circuit 10, and an optical fiber 16. The treatment light source 9 selectively emits narrow-band light having a central wavelength ranging from 610 nm to 690 nm as treatment light. The treatment light may be laser light or narrow-band LED light. Using the treatment light, a phototoxic substance can be generated at a lesion tissue in the observation object 30 where the photosensitizer is enriched, to kill cells in the lesion tissue. The treatment light drive circuit 10 is controlled by the processor 4 to turn on or turn off the treatment light source 9. The optical fiber 16 passes through an instrument passage 17 of the insertion portion 2a and protrudes from the front end portion 2c of the insertion portion 2a. An incident end surface of the optical fiber 16 receives the treatment light emitted by the treatment light source 9. The optical fiber 16 has, at a portion protruding from the front end portion 2c of the insertion portion 2a, a light emitting end from which the treatment light emitted by the treatment light source 9 can irradiate the observation object 30 in a certain direction. At the incident end surface of the optical fiber 16, an optical fiber connector, which is not shown, is arranged to detachably connect the optical fiber 16 to the treatment light source 9. In addition, the treatment light drive circuit 10 is further controlled by a treatment light control circuit, which is not shown, to adjust the amount of the treatment light emitted by the treatment light source 9.

As shown in FIG. 4, the rotation filter 12 has a disc-shaped structure with a center as a rotation axis, and the rotation filter 12 is provided with a white light illumination filter 12a and a special light illumination filter 12b. In addition, the portion of the rotation filter 12 other than the above two filters is provided with components capable of shielding light. It should be understood that in the embodiment, a distance between a center of the white light illumination filter 12a and the center of the rotation filter 12 is equal to a distance between a center of the special light illumination filter 12b and the center of the rotation filter 12. In addition, an angle between a direction from the center of the white light illumination filter 12a to the center of the rotation filter 12 and a direction from the center of the special light illumination filter 12b to the center of the rotation filter 12 may be 180 degrees, that is, the white light illumination filter 12a and the special light illumination filter 12b are arranged symmetrically around the center of the rotation filter 12 in the embodiment. It is apparent that the angle may be other degrees, such as 90 degrees.

The white light illumination filter 12a has the following transmission characteristics. In order to emit light in a wavelength range of visible light, as shown in FIG. 5, the white light illumination filter 12a is able to transmit light having a wavelength ranging from 380 nm and 700 nm, and filter out those having a wavelength greater than 700 nm.

The special light illumination filter 12b has the following transmission characteristics. In order to emit light in a wavelength band which is highly absorbed by hemoglobin (a first absorption peak of the hemoglobin ranges from 400 nm to 425 nm and a second absorption peak of hemoglobin ranges from 540 nm to 580 nm), as shown in FIG. 6, the special light illumination filter 12b is able to transmit light having a wavelength ranging from 380 nm to 600 nm, and filter out light having a wavelength greater than 600 nm which can barely be absorbed by the hemoglobin.

In addition, an illumination lens 18, a treatment light cut filter 19, an objective lens 20, and a CMOS (Complementary Metal Oxide Semiconductor device) image sensor 21 are provided at the front end portion 2c of the insertion portion 2a. With the illumination lens 18, the illumination light transmitted via the optical fiber 15 irradiate the observation object 30 at a specific angle. With the objective lens 20, an image of the observation object 30 is formed by light passing through the treatment light cut filter 19. The CMOS image sensor 21, which may be implemented by a color image sensor including a Bayer filter matrix, is arranged at an imaging position of the objective lens 20.

The treatment light cut filter 19 is arranged at a light incident side of the objective lens 20. Transmittance of the treatment light cut filter 19 for reflected treatment light from the observation object 30 is configured in a range of 0.1% to 1%, so that the intensity of the treatment light is reduced but the treatment light is not completely cut off. Therefore, it can be ensured that, in an image signal which is obtained by performing a process by the processor 4 on a signal of the observation object 30 captured by the CMOS image sensor 21, the treatment light emitted from the light emitting end of the optical fiber 16 can be observed, and the intensity of the treatment light does not cause saturation of the image signal. FIG. 8 shows light transmission characteristics of the treatment light cut filter 19 in the embodiment. FIG. 9 shows light transmission characteristics of the treatment light cut filter 19 in the embodiment, which are different from that shown in FIG. 8. With the transmission characteristics as shown in FIG. 8 (that is, the light transmittance for the wavelength band of the treatment light is in a range of 0.1% to 1%, and light transmittance for all other bands of white light is 100%), loss of white light by the treatment light cut filter 19 can be reduced, thereby improving color reproduction of an image captured using the white light. With the transmission characteristics shown in FIG. 9, design requirements on the treatment light cut filter 19 can be reduced, so that the treatment light cut filter 19 is easier to be implemented.

The CMOS image sensor 21 captures, in response to a control signal outputted by the processor 4, the image of the observation object 30 formed by light passing through the treatment light cut filter 19 and the objective lens 20, and outputs the captured image of the observation object 30 as a captured signal to the processor 4. In addition, the manipulation portion 2b of the endoscope 2 is provided with a memory 31 and a mode switcher 32. The memory 31 stores information such as a model, a serial number, and a white balance correction parameter of the endoscope 2. The mode switcher 32 is configured to output an instruction signal for switching the operation mode of the endoscope device 1 to one of the following operation modes according to a user operation. The operation modes include the white light observation mode, the special light observation mode, the white light observation along with photodynamic therapy mode, and the special light observation along with photodynamic therapy mode.

The processor 4 includes a preprocessing circuit 33, a white balance correction circuit 34, an image color correction circuit 35, an image post-processing circuit 36, a CPU 37, a mode switching circuit 38, a motor control circuit 39, a dimming circuit 40, and a CMOS controller 41.

The preprocessing circuit 33 is configured to perform preprocessing such as signal amplification and image demosaicing on the captured signal from the CMOS image sensor 21, and output an RGB image.

The white balance correction circuit 34 is controlled by the CPU 37 to read the white balance correction parameter stored in the memory 31, perform white balance correction processing on the RGB image from the preprocessing circuit 33 using the white balance correction parameter, and output a processed image.

The image color correction circuit 35 is controlled by the mode switching circuit 38 to perform image conversion processing, corresponding to the operation mode of the endoscope device 1, on the RGB image outputted from the white balance correction circuit 34.

The image post-processing circuit 36 is controlled by the mode switching circuit 38 to perform image processing such as image contrast enhancement processing on the RGB image outputted from the image color correction circuit 35 and output a processed image.

The CPU 37 accesses the information stored in the memory 31 and controls components of the processor 4 based on the information.

The mode switching circuit 38 is configured to switch, in response to the instruction signal from the mode switcher 32 and under the control of the CPU 37, the operation mode of the processor 4 to one of the following operation modes: the white light observation mode, the special light observation mode, the white light observation along with photodynamic therapy mode, and the special light observation along with photodynamic therapy mode.

The motor control circuit 39 is controlled by the mode switching circuit 38 to control the motor 13 to arrange the white light illumination filter 12a or the special light illumination filter 12b mounted on the rotation filter 12 on the exit light path of the illumination light source 7, according to the operation mode of the endoscope device 1. Thus, the light source apparatus 3 emits illumination light corresponding to the operation mode of the endoscope device 1.

In addition, the treatment light drive circuit 10 is controlled by the mode switching circuit 38 to turn on or turn off the treatment light source 9 according to the operation mode of the endoscope device 1. Specifically, the treatment light source 9 is controlled by the treatment light drive circuit 10 to be in an OFF state in the white light observation mode and the special light observation mode, and in an ON state in the white light observation along with photodynamic therapy mode and the special light observation along with photodynamic therapy mode. The treatment light emitted from the treatment light source 9 irradiates the incident end surface of the optical fiber 16. The optical fiber 16 passes through the instrument passage 17 of the insertion portion 2a, and the light emitting end of the optical fiber 16 protrudes from the front end portion 2c of the insertion portion 2a, so that the treatment light from the treatment light source 9 can irradiate the observation object 30 in a certain direction.

The dimming circuit 40 is configured to calculate, under the control of the mode switching circuit 38, a brightness value of the RGB image signal processed by the image color correction circuit 35 according to the operation mode of the endoscope device 1, calculate a difference between the brightness value and a target brightness value, and control a diaphragm amount of the diaphragm 11 according to the difference to make the light source apparatus 3 to emit illumination light with an appropriate light amount.

The CMOS controller 41 is controlled by the CPU 37 and the mode switching circuit 38 to control an electronic shutter speed, a frame rate, and an electronic gain of the CMOS image sensor 21.

The monitor 5 displays the image processed by the processor 4.

The workstation 6 is configured to perform a data archiving process on image data outputted from the processor 4.

Functions of the endoscope device 1 according to the embodiment are described below.

First, each part of the endoscope device 1 (that is, the endoscope 2, the light source apparatus 3, the processor 4, the monitor 5, and the workstation 6) is powered on and is set to be in an activated state. The operation mode of the endoscope device is set as the white light observation mode.

In the white light observation mode, the mode switching circuit 38 is configured to control, in response to the instruction signal from the mode switcher 32 and under the control of the CPU 37, various parts in the processor 4 to perform operations corresponding to the white light observation mode.

The motor control circuit 39 is controlled by the mode switching circuit 38 to control the motor 13. The motor 13 drives the rotation filter 12 to rotate to arrange the white light illumination filter 12a on the exit light path of the illumination light source 7. The illumination light filtered by the white light illumination filter 12a is condensed by the condenser lens 14, to irradiate the incident end surface of the optical fiber 15, and then transmitted via the optical fiber 15 and diffused by the illumination lens 18, to irradiate the observation object 30 at a certain irradiation angle.

In addition, the treatment light drive circuit 10 is controlled by the mode switching circuit 38 to turn off the treatment light source 9.

The CMOS controller 41 is controlled by the CPU 37 and the mode switching circuit 38 to control the electronic shutter speed, the frame rate, and the electronic gain of the CMOS image sensor 21. The CMOS image sensor 21 is configured to perform operations, in response to a control signal from the CMOS controller 41, to output an image of the observation object 30 captured in each electronic shutter time as a captured signal to the preprocessing circuit 33.

The captured signal outputted from the CMOS image sensor 21, after being subjected to pre-processing such as signal amplification and image demosaicing performed by the preprocessing circuit 33 and subjected to white balance correction performed by the white balance correction circuit 34, is inputted to the image color correction circuit 35.

The image color correction circuit 35 is controlled by the mode switching circuit 38 to perform an image color correction process on the RGB image signal outputted from the white balance correction circuit 34 based on a predetermined image color correction matrix, and output a RGB image corresponding to the white light observation mode. By performing the image color correction process, color deviation of the RGB image outputted from the white balance correction circuit 34 is corrected, where the color deviation is caused by the treatment light cut filter 19 filtering out the part of light in a red light band from the white light used for observation.

As an example, a method for calculating the predetermined image color correction matrix is described.

A reference endoscope device (not shown in the Figures), which has the same structure as the endoscope device 1 except that the treatment light cut filter 19 in the endoscope device 1 is not included, is used as a reference device for image color correction. The reference endoscope device (not shown in the Figures) includes the following main parts: a reference endoscope, a light source apparatus, a processor, a monitor, and a workstation. The reference endoscope does not include the treatment light cut filter 19 in the endoscope 2. The light source apparatus, the processor, the monitor, and the workstation has the same structures and functions as those in the endoscope device 1.

Firstly, white illumination light emitted from the light source apparatus of the reference endoscope device passes through the optical fiber 15 and the illumination lens 18, to irradiate a color block i of a standard color card. A front end face of the reference endoscope is kept parallel to the color block i at a fixed distance. A mean value of images of the color block i captured by a CMOS image sensor in the reference endoscope is recorded as $v_i=[R_i, G_i, B_i]^T$, where "T" represents an operation of matrix transposition. Under the same condition as the condition for capturing the color block i, an image of a next color block of the standard color card is captured until images of m color blocks are captured.

Then, under the same condition as the condition for capturing the images of the m color blocks by using the reference endoscope device, the CMOS image sensor 21 in the endoscope 2 of the endoscope device 1 is used to capture images of the m color blocks. A mean value of images of the color block i is recorded as $v_i'=[R_i', G_i', B_i']^T$.

A relationship between $v_i$ and $v_i'$ is established by using the following equation (1):

$$v_i = A^T_{3\times 3} \cdot v_i', \ i \in [1, m] \qquad (1)$$

where, $A^T_{3\times 3}$ is a matrix having a dimension of 3×3. Further, for the m color cards, the relationship is established as equation (2):

$$[v_1 v_2 \ldots v_m] = A^T_{3\times 3} \cdot [v_1' v_2' \ldots v_m'] \qquad (2)$$

The matrix $A^T_{3\times 3}$ is calculated by equation (3):

$$A = (I_m \cdot I_m^T)^{-1} \cdot (I_m \cdot I_{out}^T) \qquad (3)$$

In equation (3), $I_{in} = [v_i' v_2' \ldots v_m']$, $I_{out} = [v_1 v_2 \ldots v_m]$. The $A^T_{3\times 3}$ calculated by the equation (3) is stored in the image color correction circuit 35 in the processor 4 as a preset matrix parameter. The color correction process is performed on the RGB image signal outputted from the white balance correction circuit by using the equation (1), so as to eliminate the color deviation of the image signal outputted from the CMOS image sensor 21 to the processor 4 caused by the treatment light cut filter 19 in the endoscope 2.

The image post-processing circuit 36 is controlled by the mode switching circuit 38 to perform image processing such as image contrast enhancement processing on the RGB image outputted from the image color correction circuit 35 and output a processing result to the monitor 5 and the workstation 6.

The dimming circuit 40 is configured to control, based on the RGB image signal outputted from the image color correction circuit 35 and under the control of the mode switching circuit 38, the diaphragm amount of the diaphragm 11, such that the light amount of the illumination light emitted from the light source apparatus 3 is suitable for endoscope observation in the white light observation mode.

The method for controlling the diaphragm amount of the diaphragm 11 by the dimming circuit 40 is described below. In the case that the endoscope device 1 is operating in the white light observation mode, the dimming circuit 40 calculates the brightness value Y of the RGB image signal from the image color correction circuit 35 by using the following equation (4):

$$Y = 0.2126 \langle R \rangle + 0.7154 \langle G \rangle + 0.0720 \langle B \rangle \qquad (4)$$

where, <R>, <G>, and <B> respectively represent means of a R color channel, a G color channel, and a B color channel in a brightness measurement area of the RGB image.

In addition, the dimming circuit 40 calculates a difference D between the brightness value Y and a target brightness value $Y_0$, which is expressed as $D = Y - Y_0$. When the difference D is greater than 0, the dimming circuit 40 controls the diaphragm 11 to decrease the diaphragm amount by a preset adjustment amount corresponding to the difference D. When the difference D is less than 0, the dimming circuit 40 controls the diaphragm 11 to increase the diaphragm amount by a preset adjustment amount corresponding to the difference D. In this way, the light source apparatus 3 emits white illumination light with an appropriate light amount.

Then, after the above processes performed by the processor 4, the monitor 5 displays an image of an observation object 30 which reproduces a color tone of an image obtained as that the endoscope 2 does not include the treatment light cut filter 19.

In some cases, the user switches the observation mode of the endoscope device 1 from the white light observation mode to the special light observation mode by operating the mode switcher 32.

When the processor 4 is set to operate in the special light observation mode, the mode switching circuit 38 is configured to control the various parts in the processor 4, in response to the instruction signal outputted from the mode switcher 32, to perform operations corresponding to the special light observation mode.

The motor control circuit 39 is controlled by the mode switching circuit 38 to control the motor 13. The motor 13 drives the rotation filter 12 to rotate to arrange the special light illumination filter 12b on the exit light path of the illumination light source 7. The illumination light filtered by the special light illumination filter 12b is condensed by the condenser lens 14, to irradiate the incident end surface of the optical fiber 15, and then is transmitted via the optical fiber 15 and diffused by the illumination lens 18, to irradiate the observation object 30 at a certain irradiation angle.

In addition, the treatment light drive circuit 10 is controlled by the mode switching circuit 38 to turn off the treatment light source 9.

The CMOS controller 41 is controlled by the CPU 37 and the mode switching circuit 38 to control the electronic shutter speed, the frame rate, and the electronic gain of the CMOS image sensor 21. The CMOS image sensor 21 is configured to perform operations, in response to a control signal from the CMOS controller 41, to output an image of the observation object 30 captured in each electronic shutter time as a captured signal to the preprocessing circuit 33.

The captured signal outputted from the CMOS image sensor 21, after being subjected to pre-processing such as signal amplification and image demosaicing performed by the preprocessing circuit 33 and subjected to white balance correction performed by the white balance correction circuit 34, is inputted to the image color correction circuit 35.

In addition, in the special light observation mode, the white balance correction function of the endoscope device 1 is set to be in a locked state in which the function cannot be controlled by the user, and the white balance correction parameter of the white balance correction circuit 34 is set to be the same as those in the white light observation mode.

The image color correction circuit 35 is controlled by the mode switching circuit 38 to perform an image color correction process on the RGB image signal outputted from the white balance correction circuit 34 based on a predetermined image color correction matrix, and output a RGB image corresponding to the special light observation mode. By using the predetermined image color transformation matrix, for example, the G color channel and the B color channel of the RGB image signal outputted from the white balance correction circuit 34 is combined into a new RGB image signal according to preset weights. In a case that the image color correction circuit 35 performs the above image color conversion on an RGB image outputted from the white balance correction circuit 34, a new RGB image outputted from the image color correction circuit 35 no longer contains the R color channel component of the RGB image signal originally outputted from the white balance correction circuit 34. In this case, since the treatment light cut filter 19 only greatly attenuates the intensity of the treatment light having a wavelength in a red light band ranging from 610 nm to 690 nm, and has almost no effect on green light and blue light in the reflected special light from the observation object 30, the image color correction circuit 35 only performs the image color conversion process described above on the RGB image signal from the white balance correction circuit 34 in the special light observation mode, without performing the image color correction process as in the white light observation mode.

The image post-processing circuit 36 is controlled by the mode switching circuit 38 to perform image processing such as image contrast enhancement processing on the RGB image outputted from the image color correction circuit 35 and output a processing result to the monitor 5 and the workstation 6.

The dimming circuit 40 is configured to control, based on the RGB image signal outputted from the image color correction circuit 35 and under the control of the mode switching circuit 38, as in the white light observation mode, the diaphragm amount of the diaphragm 11, such that the light amount of the illumination light emitted from the light source apparatus 3 is suitable for endoscope observation in the special light observation mode.

Then, after the above processes performed in the processor 4, the monitor 5 displays an image of an observation object 30 in the special light observation mode.

In some cases, the user switches the observation mode of the endoscope device 1 from the special light observation mode to the white light observation along with photodynamic therapy mode by operating the mode switcher 32.

When the processor 4 is set to operate in the white light observation along with photodynamic therapy mode, the mode switching circuit 38 is configured to control the various parts in the processor 4, in response to the instruction signal outputted from the mode switcher 32, to perform operations corresponding to the white light observation along with photodynamic therapy mode.

The motor control circuit 39 is controlled by the mode switching circuit 38 to control the motor 13. The motor 13 drives the rotation filter 12 to rotate to arrange the white light illumination filter 12a on the exit light path of the illumination light source 7. The illumination light filtered by the white light illumination filter 12a is condensed by the condenser lens 14, to irradiate the incident end surface of the optical fiber 15, and then is transmitted via the optical fiber 15 and diffused by the illumination lens 18, to irradiate the observation object 30 at a certain irradiation angle.

In addition, the treatment light drive circuit 10 is controlled by the mode switching circuit 38 to turn on the treatment light source 9. The treatment light emitted from the treatment light source 9 irradiates the incident end surface of the optical fiber 16. The optical fiber 16 passes through the instrument passage 17 of the insertion portion 2a, and the light emitting end of the optical fiber 16 protrudes from the front end portion 2c of the insertion portion 2a, so that the treatment light from the treatment light source 9 can irradiate the observation object 30 in a certain direction (for example, from a side or a front of the treatment light cut filter 19).

The CMOS controller 41 is controlled by the CPU 37 and the mode switching circuit 38 to control the electronic shutter speed, the frame rate, and the electronic gain of the CMOS image sensor 21. The CMOS image sensor 21 is configured to perform operations, in response to a control signal from the CMOS controller 41, to output an image of the observation object 30 captured in each electronic shutter time as a captured signal to the preprocessing circuit 33.

The captured signal outputted from the CMOS image sensor 21, after being subjected to pre-processing such as signal amplification and image demosaicing performed by the preprocessing circuit 33, and subjected to white balance correction performed by the white balance correction circuit 34, is inputted to the image color correction circuit 35.

In addition, in the white light observation along with photodynamic therapy mode, the white balance correction function of the endoscope device 1 is set to be in a locked state in which the function cannot be controlled by the user, and the white balance correction parameter of the white balance correction circuit 34 stored in the memory 31 is set to be the same as those in the white light observation mode.

The image color correction circuit 35 is controlled by the mode switching circuit 38 to perform an image color correction process on the RGB image signal outputted from the white balance correction circuit 34 based on a matrix which is same as the predetermined image color correction matrix in the white light observation mode, and output a RGB image corresponding to the white light observation along with photodynamic therapy mode. The above image color correction process is used to correct color deviation of the RGB image outputted from the white balance correction circuit 34, where the color deviation is caused by the treatment light cut filter 19 filtering out part of light in a red light band from the white illumination light which is emitted from the light source apparatus 3 and then is reflected from the observation object 30.

The image post-processing circuit 36 is controlled by the mode switching circuit 38 to perform image processing such as image contrast enhancement processing on the RGB image outputted from the image color correction circuit 35 and output a processing result to the monitor 5 and the workstation 6.

The dimming circuit 40 is configured to control, based on the RGB image signal outputted from the image color correction circuit 35 and under the control of the mode switching circuit 38, the diaphragm amount of the diaphragm 11, such that the light amount of the illumination light emitted from the light source apparatus 3 is suitable for endoscope observation in the white light observation along with photodynamic therapy mode.

In addition, when the operation mode of the endoscope device 1 is in the white light observation along with photodynamic therapy mode, the treatment light source 9 is in an ON state. However, since the intensity of the treatment light emitted by the treatment light source 9 is not controlled by the processor 4, the intensity of the treatment light reflected from the observation object 30 in the image of the observation object 30 captured by the CMOS image sensor 21 is changed if the distance between the observation object 30 and the front end face 2c of the insertion portion 2a of the endoscope 2 is changed. In the case that the endoscope device 1 operates in the white light observation along with photodynamic therapy mode, if the dimming circuit 40 performs dimming in the same way as the way in the white light observation mode, an undesired effect of image flicker will be caused.

In view of the above, in the case that the endoscope device 1 operates in the white light observation along with photodynamic therapy mode, the dimming circuit 40 calculates the brightness value Y of the RGB image signal outputted from the image color correction circuit 35 by using, for example, the G channel or the B channel of the RGB image signal. The dimming circuit 40 calculates a difference D between the brightness value Y and a target brightness value $Y_0$, which is expressed as $D=Y-Y_0$. When the difference D is greater than 0, the dimming circuit 40 controls the diaphragm 11 to decrease the diaphragm amount by a preset adjustment amount corresponding to the difference D. When the difference D is less than 0, the dimming circuit 40 controls the diaphragm 11 to increase the diaphragm amount by a preset adjustment amount corresponding to the difference D. In this way, the light source apparatus 3 emits white illumination light with an appropriate light amount.

Then, after the above processes performed by the processor 4, the monitor 5 displays an image of an observation object 30 in the white light observation along with photodynamic therapy mode.

In some cases, the user switches the observation mode of the endoscope device 1 from the white light observation along with photodynamic therapy mode to the special light observation along with photodynamic therapy mode by operating the mode switcher 32.

When the processor 4 is set to operate in the special light observation along with photodynamic therapy mode, the mode switching circuit 38 is configured to control various parts in the processor 4, in response to the instruction signal outputted from the mode switcher 32, to perform operations corresponding to the special light observation along with photodynamic therapy mode.

The motor control circuit 39 is controlled by the mode switching circuit 38 to control the motor 13. The motor 13 drives the rotation filter 12 to rotate to arrange the special light illumination filter 12b on the exit light path of the illumination light source 7. The illumination light filtered by the special light illumination filter 12b is condensed by the condenser lens 14, to irradiate the incident end surface of the optical fiber 15, and then is transmitted via the optical fiber 15 and diffused by the illumination lens 18, to irradiate the observation object 30 at a certain irradiation angle.

In addition, the treatment light drive circuit 10 is controlled by the mode switching circuit 38 to turn on the treatment light source 9. The treatment light emitted from the treatment light source 9 irradiates the incident end surface of the optical fiber 16. The optical fiber 16 passes through the instrument passage 17 of the insertion portion 2a, and the light emitting end of the optical fiber 16 protrudes from the front end portion 2c of the insertion portion 2a, so that the treatment light from the treatment light source 9 can irradiate the observation object 30 in a certain direction (for example, from a side or a front of the treatment light cut filter 19).

The CMOS controller 41 is controlled by the CPU 37 and the mode switching circuit 38 to control the electronic shutter speed, the frame rate, and the electronic gain of the CMOS image sensor 21. The CMOS image sensor 21 is configured to perform operations, in response to a control signal from the CMOS controller 41, to output an image of the observation object 30 captured in each electronic shutter time as a captured signal to the preprocessing circuit 33.

The captured signal outputted from the CMOS image sensor 21, after being subjected to pre-processing such as signal amplification and image demosaicing performed by the preprocessing circuit 33, and subjected to white balance correction performed by the white balance correction circuit 34, is inputted to the image color correction circuit 35.

In addition, in the special light observation along with photodynamic therapy mode, the white balance correction function of the endoscope device 1 is set to be in a locked state in which the function cannot be controlled by the user, and the white balance correction parameter of the white balance correction circuit 34 is set to be the same as those in the white light observation mode.

The image color correction circuit 35 is controlled by the mode switching circuit 38 to perform an image color correction process on the RGB image signal outputted from the white balance correction circuit 34 based on a predetermined image color correction matrix which is same as the predetermined image color correction matrix in the special light observation mode, and outputs a RGB image corresponding to the special light observation along with photodynamic therapy mode.

The image post-processing circuit 36 is controlled by the mode switching circuit 38 to perform image processing such as image contrast enhancement processing on the RGB image outputted from the image color correction circuit 35 and output a processing result to the monitor 5 and the workstation 6.

The dimming circuit 40 is configured to control, in response to the RGB image signal outputted from the image color correction circuit 35 and under the control of the mode switching circuit 38, the diaphragm amount of the diaphragm 11, such that the light amount of the illumination light emitted from the light source apparatus 3 is suitable for endoscope observation in the special light observation along with photodynamic therapy mode.

In the case that the endoscope device 1 is operating in the special light observation along with photodynamic therapy mode, the dimming circuit 40 calculates the brightness value Y of the RGB image signal outputted from the image color correction circuit 35 using the above equation (4), and calculates a difference D between the brightness value Y and a target brightness value $Y_0$, which is expressed as $D=Y-Y_0$. When the difference D is greater than 0, the dimming circuit 40 controls the diaphragm 11 to decrease the diaphragm amount by a preset adjustment amount corresponding to the difference D. When the difference D is less than 0, the dimming circuit 40 controls the diaphragm 11 to increase the diaphragm amount by a preset adjustment amount corresponding to the difference D. In this way, the light source apparatus 3 emits illumination light for special light observation with an appropriate light amount.

In addition, in the case that the endoscope device 1 operates in the special light observation along with photodynamic therapy mode, if the image color correction circuit 35 performs the above image color conversion on an RGB image outputted from the white balance correction circuit 34, a new RGB image outputted from the image color correction circuit 35 no longer contains the R color channel component of the RGB image signal originally outputted from the white balance correction circuit 34. Therefore, in calculating the brightness value Y of the image signal outputted from the image color correction circuit 35 by using the equation (4) and performing the dimming process, the change in the distance between the observation object 30 and the front end face 2c of the insertion portion 2a of the endoscope 2 will not cause the image flicker.

Then, after the above process performed by the processor 4, the monitor 5 displays an image of an observation object 30 in the special light observation along with photodynamic therapy mode.

Figure 10:
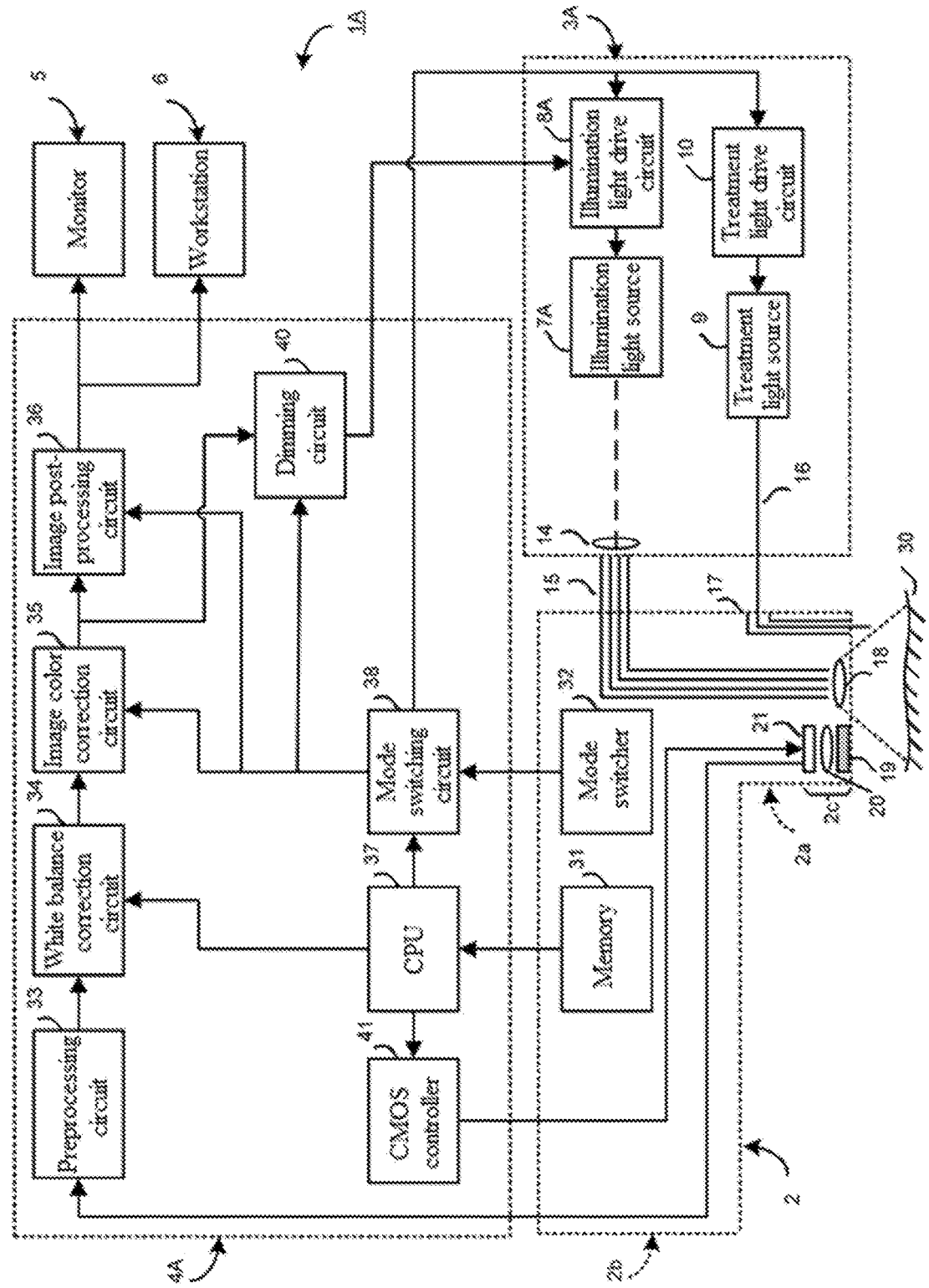
FIG. 10 is a schematic diagram of a main structure of an endoscope device according to another embodiment of the present disclosure.
Figure 11:
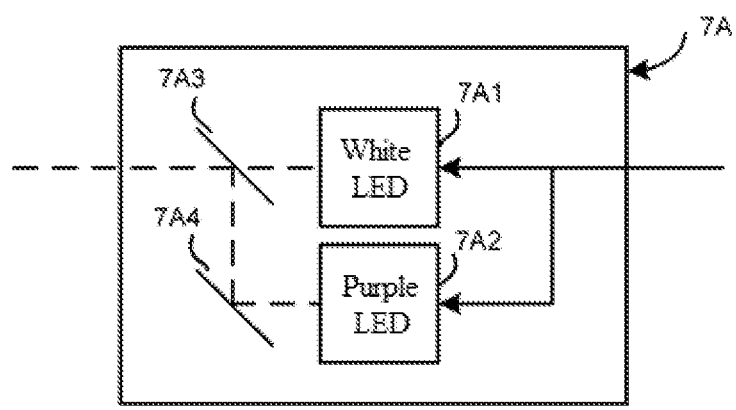
FIG. 11 is a schematic diagram of a main structure of the illumination light source shown in FIG. 10 according to an embodiment.

Based on the above embodiments, an endoscope device is provided according to another embodiment of the present disclosure. Reference is made to FIG. 10 and FIG. 11, which show technical solutions in the embodiment of the present disclosure. FIG. 10 is a schematic diagram of a main structure of an endoscope device according to another embodiment of the present disclosure. FIG. 11 is a schematic diagram of a main structure of the illumination light source shown in FIG. 10 according to an embodiment.

It is noted that, the structure of the endoscope device according to this embodiment is similar to that of the endoscope device according to the above embodiments, and only the difference in structures or functions are described in detail below.

As shown in FIG. 10, the endoscope device 1A according to this embodiment includes the following main parts: an endoscope 2, a light source apparatus 3A, a processor 4A, a monitor 5, and a workstation 6. The light source apparatus 3A emits treatment light for treatment, and emits illumination light which is formed by a combination of light emitted by two or more light sources having different wavelength bands. The processor 4A does not include the motor control circuit 39 included in the processor 4.

The light source apparatus 3A includes an illumination light source 7A, an illumination light drive circuit 8A, and a condenser lens 14. The illumination light source 7A emits illumination light which is formed by a combination of light emitted by two or more light sources having different wavelength bands. For example, as shown in FIG. 11, the illumination light source 7A may include a white LED 7A1, a purple LED 7A2, a reflecting mirror 7A4, and a dichroic mirror 7A3. The purple LED 7A2 has a wavelength band ranging from 400 nm to 430 nm. The reflecting mirror 7A4 and the dichroic mirror 7A3 combine the light emitted by the white LED 7A1 and the purple LED 7A2. The illumination light drive circuit 8A is controlled by the processor 4A to control amounts of light in different wavelength bands emitted by the illumination light source 7A. The condenser lens 14 condenses the illumination light emitted from the illumination light source 7A and makes the condensed illumination light irradiate an incident end surface of the optical fiber 15 which is connected to the light source apparatus 3A. The light source apparatus 3A does not include the diaphragm 11, the rotation filter 12, and the motor 13 included in the light source apparatus 3.

In addition, the light source apparatus 3A further includes a treatment light source 9, a treatment light drive circuit 10, and an optical fiber 16. The treatment light source 9 selectively emits narrow-band light having a central wavelength ranging from 610 nm to 690 nm as treatment light. The treatment light may be laser light or narrow-band LED light. Using the treatment light, a phototoxic substance can be generated at a lesion tissue in the observation object 30 where the photosensitizer is enriched, to kill cells in the lesion tissue. The treatment light drive circuit 10 is controlled by the processor 4A to turn on or turn off the treatment light source 9. The optical fiber 16 passes through an instrument passage 17 of the insertion portion 2a and protrudes from the front end portion 2c of the insertion portion 2a. An incident end surface of the optical fiber 16 receives the treatment light emitted by the treatment light source 9. The optical fiber 16 has, at a portion protruding from the front end portion 2c of the insertion portion 2a, a light emitting end from which the treatment light emitted by the treatment light source 9 can irradiate the observation object 30 in a certain direction. At the incident end surface of the optical fiber 16, an optical fiber connector, which is not shown, is arranged to detachably connect the optical fiber 16 to the treatment light source 9. In addition, the treatment light drive circuit 10 is further controlled by a treatment light control circuit, which is not shown, to adjust the amount of the treatment light emitted by the treatment light source 9.

The processor 4A includes a preprocessing circuit 33, a white balance correction circuit 34, an image color correction circuit 35, an image post-processing circuit 36, a CPU 37, a mode switching circuit 38, a dimming circuit 40, and a CMOS controller 41.

The mode switching circuit 38 is configured to control, in response to the instruction signal from the mode switcher 32 and under the control of the CPU 37, the illumination light drive circuit 8A and the treatment light drive circuit 10 to switch the operation mode of the processor 4A to one of the following operation modes: a white light observation mode, a special light observation mode, a white light observation along with photodynamic therapy mode, and a special light observation along with photodynamic therapy mode.

The dimming circuit 40 is configured to calculate, under the control of the mode switching circuit 38, a brightness value of the RGB image signal processed by the image color correction circuit 35 according to the operation mode of the endoscope device 1A, calculate a difference between the brightness value and a target brightness value, and control a driving current of the illumination light drive circuit 8A based on the difference to make the illumination light source 7A emit illumination light with an appropriate light amount corresponding to the operation mode of the endoscope device 1A.

It can be seen that the difference between the endoscope device 1A according to this embodiment and the endoscope device 1 according to the above embodiments mainly lies in the illumination light source 7A and the illumination light drive circuit 8A in the light source apparatus 3A, and the light amount control method thereof. The functions of the endoscope device 1A according to this embodiment are substantially the same as those of the endoscope device 1 according to the above embodiments, which are not repeated herein. Only the function of the light amount control of the illumination light drive circuit 8A is described below.

In providing illumination light, the illumination light drive circuit 8A may, under the control of the mode switching circuit 38, control the illumination light source 7A to emit illumination light in different wavelength bands, according to an emitting light power ratio corresponding to the selected operation mode. For example, as shown in FIG. 11, a ratio of the amount of light emitted by the white LED 7A1 to the amount of light emitted by the purple LED 7A2 is controlled in accordance with the emitting light power ratio corresponding to the selected operation mode. The illumination light emitted by the illumination light source 7A is condensed by the condenser lens 14, to irradiate the incident end surface of the optical fiber 15, and then is transmitted via the optical fiber 15 and diffused by the illumination lens 18, to irradiate the observation object 30 at a certain irradiation angle.

In adjusting light amount in response to the control signal of the dimming circuit 40, the illumination light drive circuit 8A increases or decreases driving currents provided to the light sources having different wavelength bands in the illumination light source 7A by a preset adjustment amount, to increases or decreases the amount of light emitted by the illumination light source 7A. Thus, the light source apparatus 3A emits illumination light with an appropriate light amount under the control of the dimming circuit 40.

In addition, the technical solutions of the present disclosure are not limited to the above embodiments, and various changes and applications can be made without departing from the spirit of the present disclosure. For example, in the light source apparatus 3A shown in FIG. 10, the illumination light source 7A may include laser light sources of four colors of red, green, blue, and purple, or include LED light sources of four colors of red, green, blue and purple, or include mixed laser light sources and LED light sources having different wavelengths. In addition, the treatment light source 9 may be combined with the illumination light source 7 or the illumination light source 7A, and the treatment light is transmitted via the optical fiber 15 and diffused by the illumination lens 18, to irradiate the observation object 30.

The technical solutions disclosed in the above embodiments have the following beneficial effects.

In a first aspect, a treatment light cut filter is arranged between the object and the endoscope imaging section according to the present disclosure, and the transmittance of the treatment light cut filter for the treatment light ranges from 0.1% to 1%. Therefore, image overexposure is avoided, thereby ensuring real-time visualization in the photodynamic therapy process. Also, according to the optical filtering characteristics of the light cut filter, an appropriate amount of the PDT treatment light can transmit through the light cut filter to be received by the image sensor in the endoscope imaging section. Therefore, the medical personnel can observe, in the image displayed on the monitor, the treatment light emitted from the light emitting end surface of the optical fiber dedicated for PDT treatment, to determine that the optical fiber dedicated for PDT treatment operates normally (for example, the optical fiber is unbroken and the treatment light is coupled normally to the optical fiber) during the PDT process.

In a second aspect, with the technical solutions in the present disclosure, the PDT treatment light can irradiate continuously without changing the clinical irradiation time and irradiation intensity of the PDT treatment light. Compared with the technical solutions of using signal timing control, the treatment time is shortened, which ensures the treatment effect, and an optical signal can be captured at an appropriate electronic shutter speed, which ensures brightness and signal-to-noise ratio of a captured image.

In a third aspect, an endoscope device having multiple operation modes is provided according to the present disclosure, enabling users to perform operations of white light observation, special light observation, white light observation along with photodynamic therapy, or special light observation along with photodynamic therapy, according to actual needs.

In a fourth aspect, to solve the problem that the color of the captured image is different from the color of the image under normal white light due to the treatment light cut filter filtering out the light in the treatment light band (a wavelength or all wavelengths in the wavelength range of 610 nm to 690 nm), an image color correction method under white light illumination is provided. With the method, the image captured by the endoscope device according to the present disclosure under white light illumination is displayed in a color similar to the color of the image captured by a common endoscope device under the white light illumination, so that the observer will not feel discomfort due to deviations in the color of the image.

In a fifth aspect, a method for controlling the amount of light emitted by the light source in different operation modes of the endoscope device is provided according to the present disclosure, achieving quantified control on the image brightness in different operation modes, and avoiding overexposure, over-dark, or flickering of the image.

In a sixth aspect, with the method that the PDT treatment light is transmitted via a PDT treatment dedicated optical fiber to enter the body cavity through a surgical instrument passage of the endoscope according to the present disclosure, the medical personnel can choose a PDT treatment dedicated optical fiber according to the location, shape, and distribution of a tumor tissue. Compared with the method that the PDT treatment light and the illumination light share an optical fiber of the endoscope and are emitted divergently at a certain angle from an illumination window at an end of the endoscope, the method according to the present disclosure not only has better applicability to ensure the therapeutic effect, but also can avoid the risk of burning biological tissue due to overheating of the end of the endoscope.

The embodiments in the specification are described in a progressive manner. Each of the embodiments is mainly focused on its differences from other embodiments, and references may be made one to another for the same or similar parts. The device disclosed in the embodiment corresponds to the method disclosed in the embodiment, and thus is described relatively simply. For detailed description of the device, reference may be made to the related description of the method.

It is known by those skilled in the art that, units and algorithm steps in each example described in conjunction with the embodiments disclosed herein can be implemented by electronic hardware, computer software, or a combination thereof. In order to clearly illustrate interchangeability of the hardware and the software, steps and composition of each embodiment have been described generally in view of functions in the above specification. Whether the function is executed in a hardware way or in a software way depends on applications of the technical solution and design constraint conditions. Those skilled in the art can use different methods for different applications to realize the described functions, which are not considered to be beyond the scope of the present disclosure.

The steps of the methods or algorithms described in conjunction with the embodiments of the present disclosure can be implemented with hardware, software modules executed by a processor, or a combination thereof. The software modules may reside in a Random Access Memory (RAM), a memory, a Read Only Memory (ROM), an Electrically Programmable ROM, an Electrically-Erasable Programmable ROM, a register, a hard disk, a removable disk drive, CD-ROM, or other types of storage media well known in the technical field.

Finally, it should be further noted that the relationship terminologies such as "first", "second" and the like are only used herein to distinguish one entity or operation from another, rather than to necessitate or imply that the actual relationship or order exists between the entities or operations. Furthermore, terms of "include", "comprise" or any other variants are intended to be non-exclusive. Therefore, a process, method, article or device including a plurality of elements includes not only the elements but also other elements that are not enumerated, or also include the elements inherent to the process, method, article or device. Unless expressively limited otherwise, the statement "comprising (including) a . . . " does not exclude the case that other same elements may exist in the process, method, article or device.

The endoscope device provided by the present disclosure is described in detail above. The principles and implementations of the present disclosure are clarified using specific embodiments herein. The above description of the embodiments is only intended to help understanding the functions of the present disclosure and the key concept thereof. In addition, changes can be made to the specific embodiments and the application scope by those skilled in the art based on the concept of the present disclosure. In summary, the specification should not be interpreted as limitation to the technical solutions in the present disclosure.

The invention claimed is:

1. An endoscope device, comprising:
   a first light source section, configured to project illumination light to an object;
   a second light source section, configured to project treatment light to the object;

an imaging section, configured to capture an image of the object using reflected light from the object; and a light cut filter, arranged between the object and the imaging section, wherein the light cut filter has a transmittance greater than or equal to 0.1% and less than or equal to 1% for the treatment light.

2. The endoscope device according to claim 1, wherein the second light source section comprises:

a laser light source, configured to project red laser light to the object, wherein the red laser light has a central wavelength ranging from 610 nm to 690 nm; or a Light Emitting Diode (LED) light source, configured to project red narrow-band LED light to the object, wherein the red narrow-band LED light has a central wavelength ranging from 610 nm to 690 nm.

3. The endoscope device according to claim 1, wherein the first light source section comprises:

a white light source, configured to project white light to the object, and a special light source, configured to project special light to the object, wherein, a wavelength of the white light is in a wavelength range of visible light, and a wavelength of the special light is in a wavelength range corresponding to an absorption peak of hemoglobin.

4. The endoscope device according to claim 3, further comprising:

an observation mode switcher, and a light source control component, configured to control the first light source section and the second light source section according to an operation mode selected by a user using the observation mode switcher, wherein the operation mode comprises a white light observation mode, a special light observation mode, a white light observation along with photodynamic therapy mode, or a special light observation along with photodynamic therapy mode.

5. The endoscope device according to claim 3, further comprising:

an image color correction section, configured to perform a color correction process on the image captured by the imaging section based on a predetermined color correction matrix when the first light source section projects the white light to the object, wherein the predetermined color correction matrix is calculated by a least squares algorithm based on a difference between a first color expression result and a second color expression result, the first color expression result being obtained based on an image of the object which is captured using white light filtered by the light cut filter, and the second color expression result being obtained based on an image of the object which is captured directly using the white light.

6. The endoscope device according to claim 1, further comprising:

a dimming circuit, configured to determine a brightness value of a current image captured by the imaging section, and adjust a light source parameter of the first light source section based on a difference between the brightness value and a predetermined brightness value; and/or an imaging controller, configured to determine a brightness value of a current image captured by the imaging section, and adjust an imaging parameter of the imaging section based on a difference between the brightness value and a predetermined brightness value.

7. The endoscope device according to claim 1, further comprising:

a dedicated optical fiber, arranged between the second light source section and the object and configured to transmit the treatment light.

8. The endoscope device according to claim 7, wherein the dedicated optical fiber passes through a surgical instrument passage of the endoscope device and protrudes from a front end face of an insertion portion of the endoscope device.

9. The endoscope device according to claim 7, wherein the second light source section further comprises:

a verification light source, configured to generate verification light having a wavelength different from a wavelength of the treatment light to verify whether the dedicated optical fiber is capable of transmitting light normally.

10. The endoscope device according to claim 1, wherein the first light source section comprises a white light source configured to project white light to the object, and a wavelength of the white light is in a wavelength range of visible light, and the endoscope device further comprises:

an observation mode switcher, a light source control component, configured to control the first light source section and the second light source section according to an operation mode selected by a user using the observation mode switcher, wherein the operation mode comprises a white light observation mode or a white light observation along with photodynamic therapy mode, and a dimming circuit, configured to calculate, in accordance with the selected operation mode, a brightness value of the image captured by the imaging section, and adjust a light source parameter of the first light source section based on a difference between the calculated brightness value and a predetermined brightness value, wherein a brightness calculating method used in the white light observation mode is different from a brightness calculating method used in the white light observation along with photodynamic therapy mode.

11. The endoscope device according to claim 10, wherein the first light source section further comprises a special light source for projecting special light to the object, wherein a wavelength of the special light is in a wavelength range corresponding to an absorption peak of hemoglobin; and the operation mode further comprises a special light observation mode or a special light observation along with photodynamic therapy mode.

12. The endoscope device according to claim 11, further comprising:

an image color correction circuit, configured to perform an image conversion process corresponding to the selected operation mode on the image captured by the imaging section.

13. The endoscope device according to claim 12, wherein the image color correction circuit is configured to perform, when the selected operation mode is the white light observation mode or the white light observation along with photodynamic therapy mode, a color correction process on the image captured by the imaging section based on a predetermined color correction matrix, wherein the predetermined color correction matrix is calculated by a least squares algorithm based on a difference between a first color expression result and a second color expression result, the first color expression result being obtained based on an image of the object which is captured using white light filtered by the light cut filter, and the second color expression result being obtained based on an image of the object which is captured directly using the white light.

14. The endoscope device according to claim 12, wherein the image color correction circuit is configured to perform, when the selected operation mode is the special light observation mode or the special light observation along with photodynamic therapy mode, a color transformation process on the image captured by the imaging section using a predetermined color transformation matrix, wherein the predetermined color transformation matrix is used to combine a G color channel and a B color channel of the image captured by the imaging section according to preset weights to form a new image.

15. The endoscope device according to claim 10, further comprising:

a dedicated optical fiber, arranged between the second light source section and the object and configured to transmit the treatment light.

16. The endoscope device according to claim 15, wherein the dedicated optical fiber passes through a surgical instrument passage of the endoscope device and protrudes from a front end face of an insertion portion of the endoscope device.

17. The endoscope device according to claim 16, wherein the second light source section further comprises:

a verification light source, configured to generate verification light having a wavelength different from a wavelength of the treatment light to verify whether the dedicated optical fiber is capable of transmitting light normally.

18. The endoscope device according to claim 17, wherein the wavelength of the verification light generated by the verification light source is less than the wavelength of the treatment light.

* * * * *